United States Patent
Im et al.

(10) Patent No.: US 11,846,882 B2
(45) Date of Patent: Dec. 19, 2023

(54) METHODS FOR MANUFACTURING HIGH-DENSITY NEURAL PROBES HAVING VARIOUS FORMS

(71) Applicant: KOREA INSTITUTE OF SCIENCE AND TECHNOLOGY, Seoul (KR)

(72) Inventors: Maesoon Im, Seoul (KR); Byung Chul Lee, Seoul (KR); Young Jun Yoon, Seoul (KR); Jin Soo Park, Seoul (KR); Seung Min Kwak, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 716 days.

(21) Appl. No.: 16/923,965

(22) Filed: Jul. 8, 2020

(65) Prior Publication Data
US 2021/0240076 A1    Aug. 5, 2021

(30) Foreign Application Priority Data

Jan. 31, 2020   (KR) ........................ 10-2020-0011815

(51) Int. Cl.
*G03F 7/004*   (2006.01)
*A61N 1/05*    (2006.01)
*A61B 5/24*    (2021.01)

(52) U.S. Cl.
CPC .............. *G03F 7/0041* (2013.01); *A61B 5/24* (2021.01); *A61N 1/0529* (2013.01); *A61B 2562/125* (2013.01)

(58) Field of Classification Search
CPC ... G03F 7/0041; A61B 5/24; A61B 2562/125; A61B 5/262; A61B 2562/0209;
(Continued)

(56) References Cited

U.S. PATENT DOCUMENTS 5,928,207 A * 7/1999 Pisano ................. A61B 5/1473
                                              606/222
6,187,210 B1 * 2/2001 Lebouitz ............... A61B 5/296
                                                216/2
(Continued)

FOREIGN PATENT DOCUMENTS

JP   2014166352 A  *  9/2014  ........ A61M 37/0015
KR   10-1159697 B1     6/2012
(Continued)

OTHER PUBLICATIONS

Li, Yan, "Fabrication of sharp silicon hollow microneedles by deep-reactive ion etching towards minimally invasive diagnostics", Microsystems & Nanoengineering ( 2019)5 :41 (Year: 2019).*

*Primary Examiner* — Peter Dungba Vo
*Assistant Examiner* — Jose K Abraham
(74) *Attorney, Agent, or Firm* — Goldilocks Zone IP Law

(57) ABSTRACT

Disclosed is a method for manufacturing a high-density neural probe including needles having various forms. The method, in which only a photolithography process and an etching process are used, simplifies a manufacturing process of the neural probe, minimizes changes in the characteristics of the neural probe depending on process equipment or conditions, and may thus ensure a high yield, thereby being advantageous in terms of commercialization. In addition, various forms of needles may be manufactured depending on the shape of patterns included in a mask, the height of the needles may be controlled by adjusting the size of the patterns and the gap between the patterns, and thereby, a neural probe having a plurality of needles having different heights may be manufactured.

5 Claims, 8 Drawing Sheets

(58) Field of Classification Search
CPC .. A61N 1/0529; A61N 1/0531; A61N 1/3605; A61N 1/36125
See application file for complete search history.

(56) References Cited

U.S. PATENT DOCUMENTS

| | | | |
|---|---|---|---|
| 7,241,689 B2 | 7/2007 | Kim et al. | |
| 7,429,333 B2 * | 9/2008 | Chiou | B29C 33/40 216/11 |
| 8,043,250 B2 * | 10/2011 | Xu | B82Y 5/00 604/22 |
| 8,048,017 B2 * | 11/2011 | Xu | A61B 17/205 604/22 |
| 8,148,264 B2 * | 4/2012 | Henry | H01L 21/3065 438/668 |
| 8,255,061 B2 * | 8/2012 | Perlin | A61N 1/0529 600/377 |
| 8,865,288 B2 | 10/2014 | Bhandari et al. | |
| 8,883,015 B2 * | 11/2014 | Kendall | H01J 37/32009 216/2 |
| 9,005,548 B2 * | 4/2015 | Henry | B01J 19/0046 422/551 |
| 9,283,365 B2 * | 3/2016 | Kendall | A61K 9/0021 |
| 9,390,936 B2 * | 7/2016 | Henry | B81C 1/00111 |
| 2009/0093776 A1 * | 4/2009 | Yue | A61B 5/150984 216/41 |
| 2009/0318824 A1 | 12/2009 | Nishida et al. | |
| 2010/0215543 A1 * | 8/2010 | Henry | B81C 1/00111 430/296 |
| 2011/0223542 A1 * | 9/2011 | Kendall | H01J 37/32009 430/320 |
| 2013/0338632 A1 * | 12/2013 | Kaplan | A61M 5/158 604/173 |
| 2015/0050746 A1 * | 2/2015 | Henry | H01L 21/3086 430/296 |
| 2015/0224294 A1 * | 8/2015 | Kendall | B81C 1/00111 204/192.15 |
| 2016/0280537 A1 * | 9/2016 | Henry | B81C 1/00111 |
| 2018/0217080 A1 | 8/2018 | Kinser | |

FOREIGN PATENT DOCUMENTS

| | | | |
|---|---|---|---|
| KR | 10-1209403 B1 | 12/2012 | |
| KR | 10-1688739 B1 | 12/2016 | |
| WO | WO-2009064164 A2 * | 5/2009 | ........ A61M 37/0015 |

* cited by examiner

[FIG. 1]
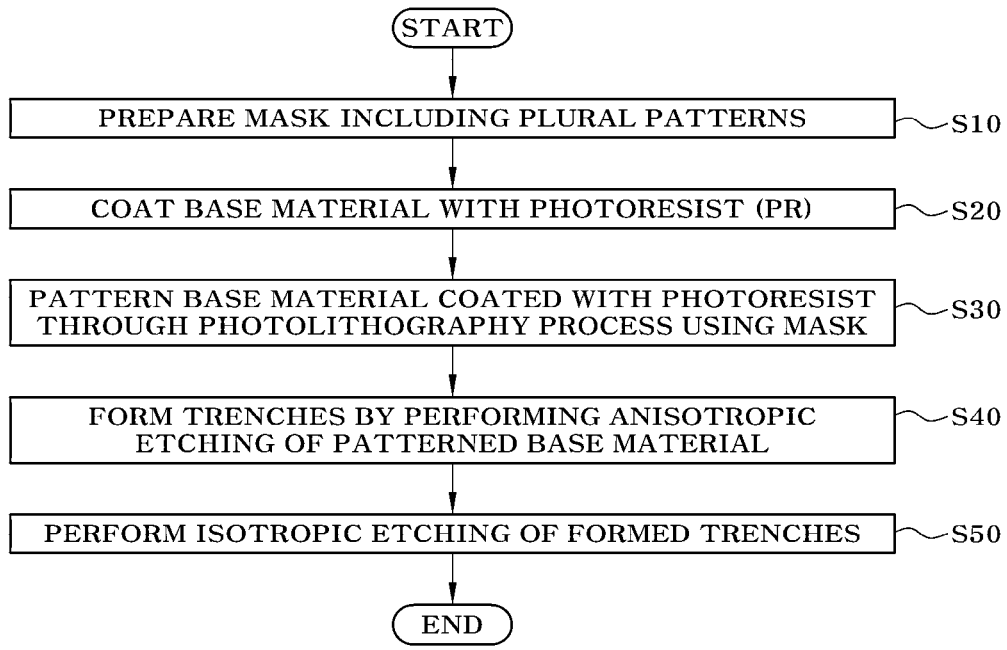
[FIG. 2]
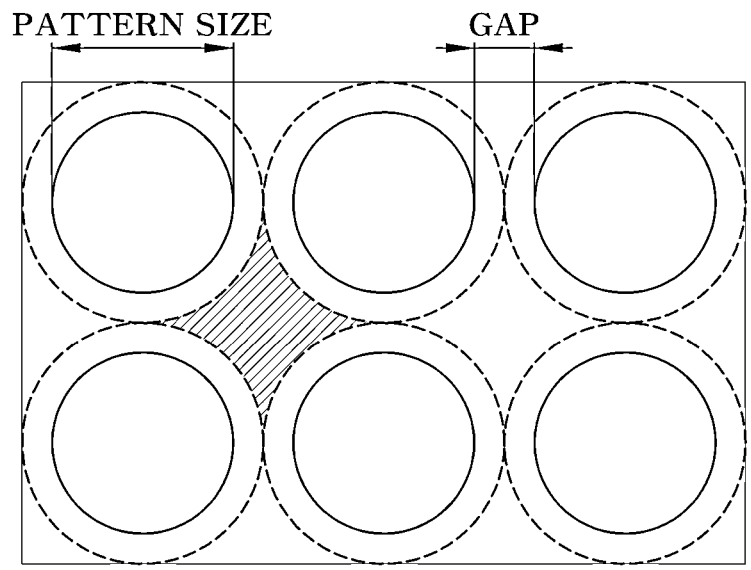

[FIG. 3A]
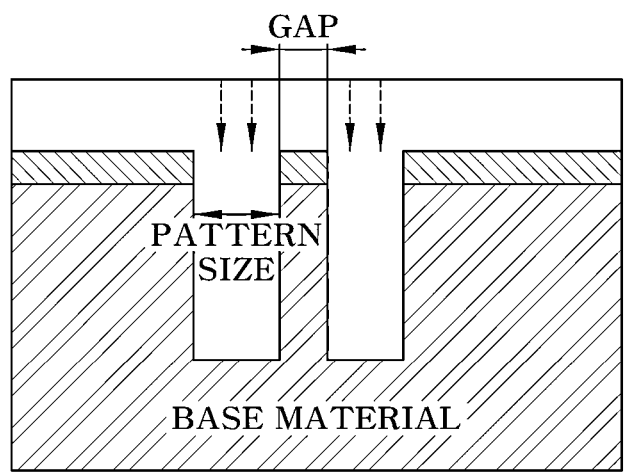
[FIG. 3B]
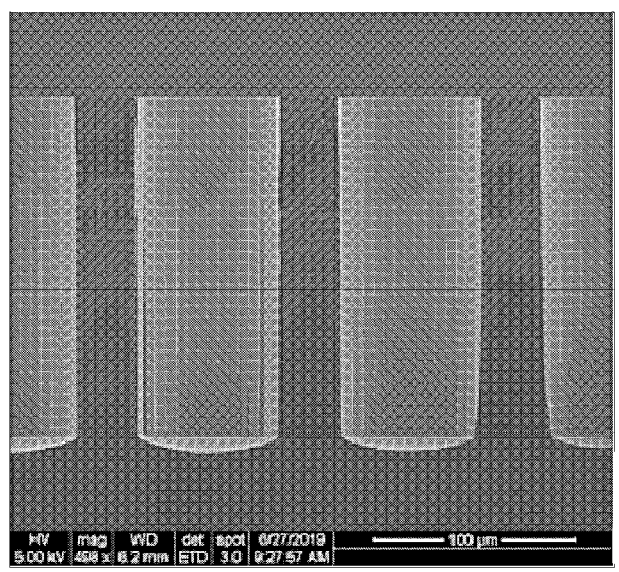

[FIG. 4A]
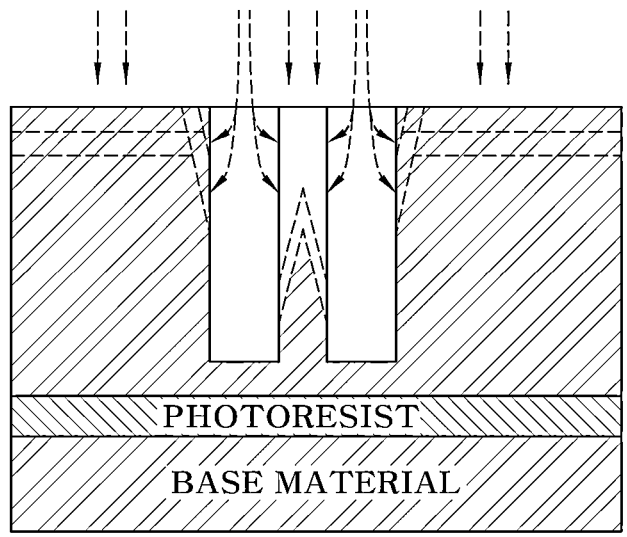
[FIG. 4B]
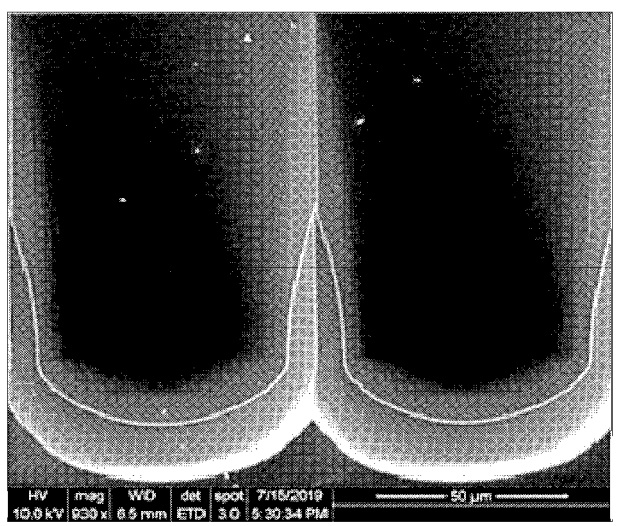

[FIG. 5]
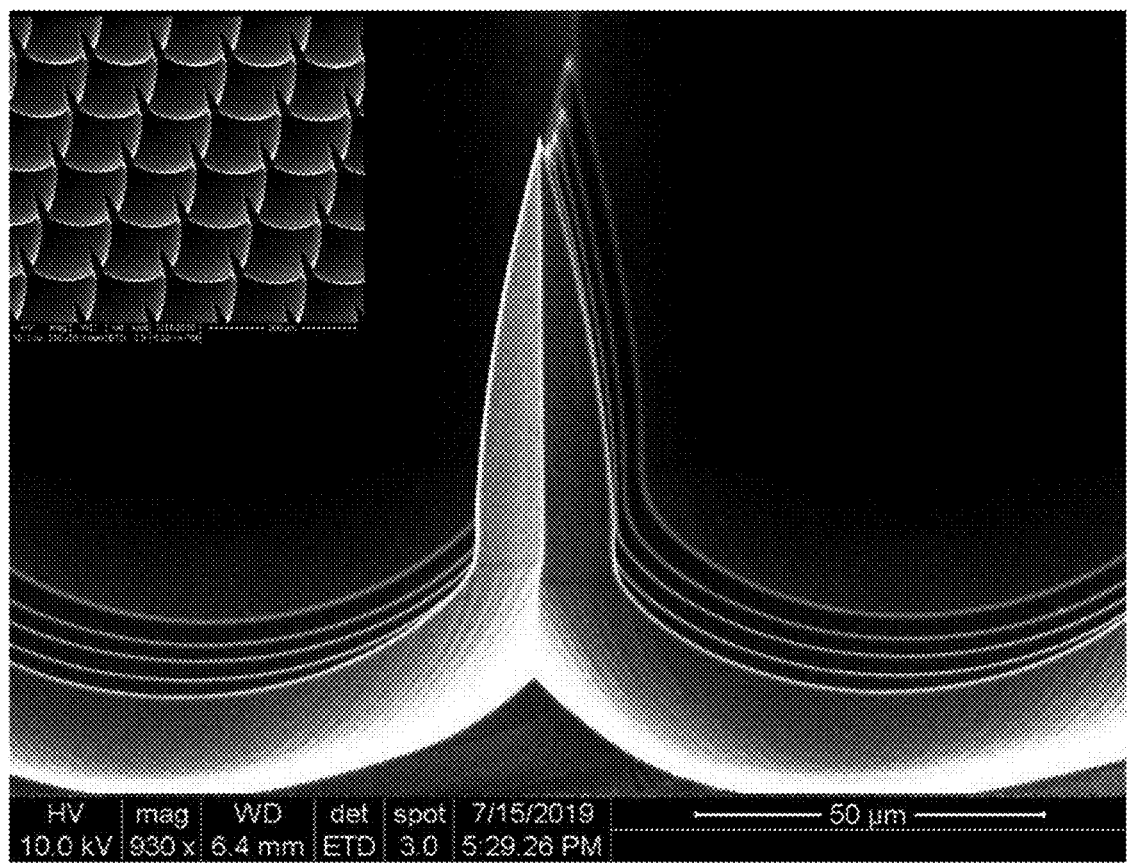

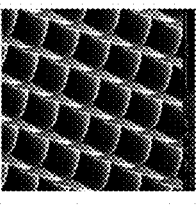
[FIG. 6]

[FIG. 7A]
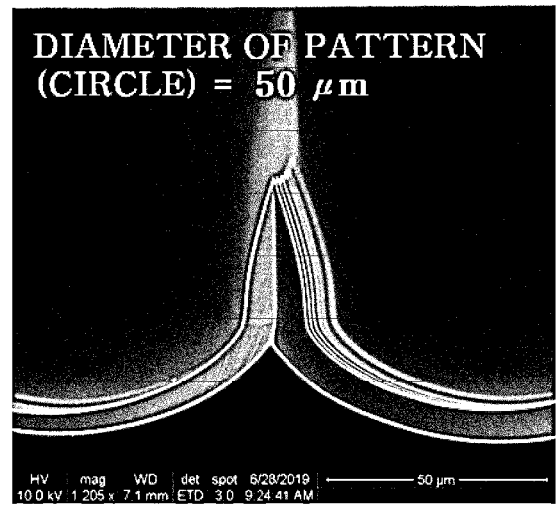
[FIG. 7B]
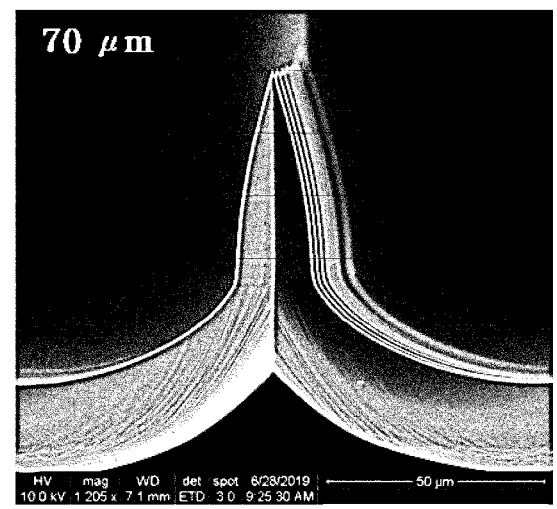

[FIG. 7C]
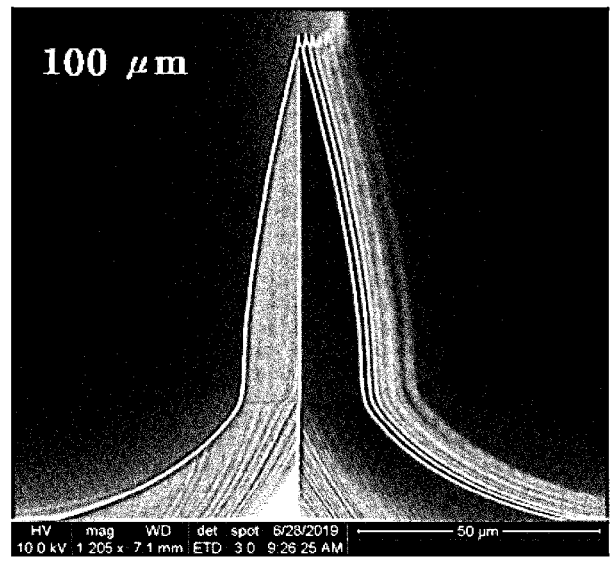
[FIG. 8]
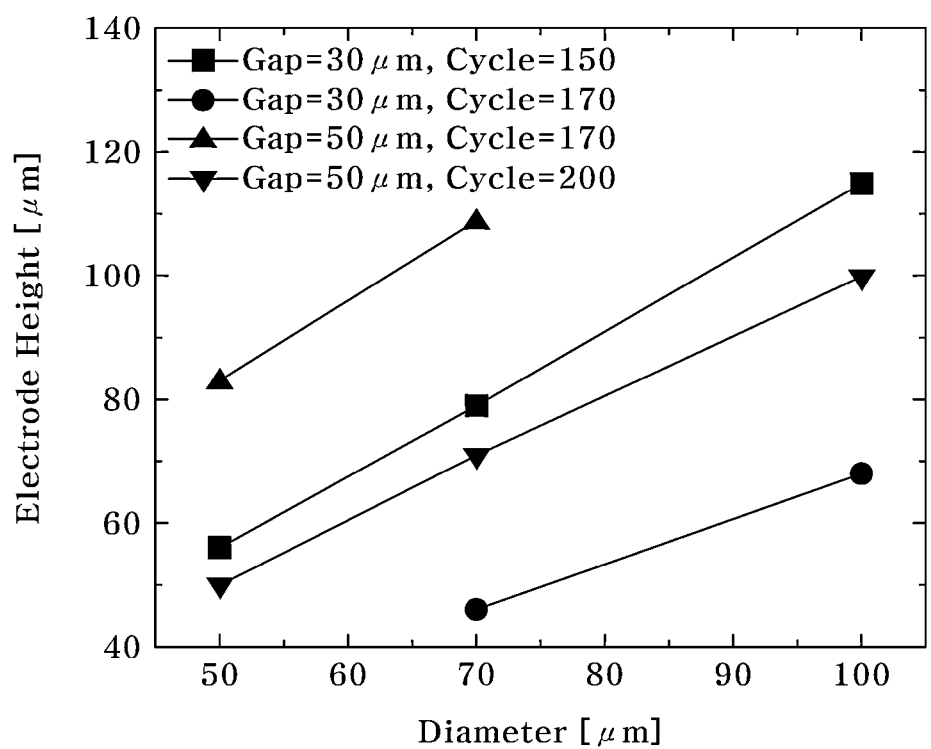

[FIG. 9]
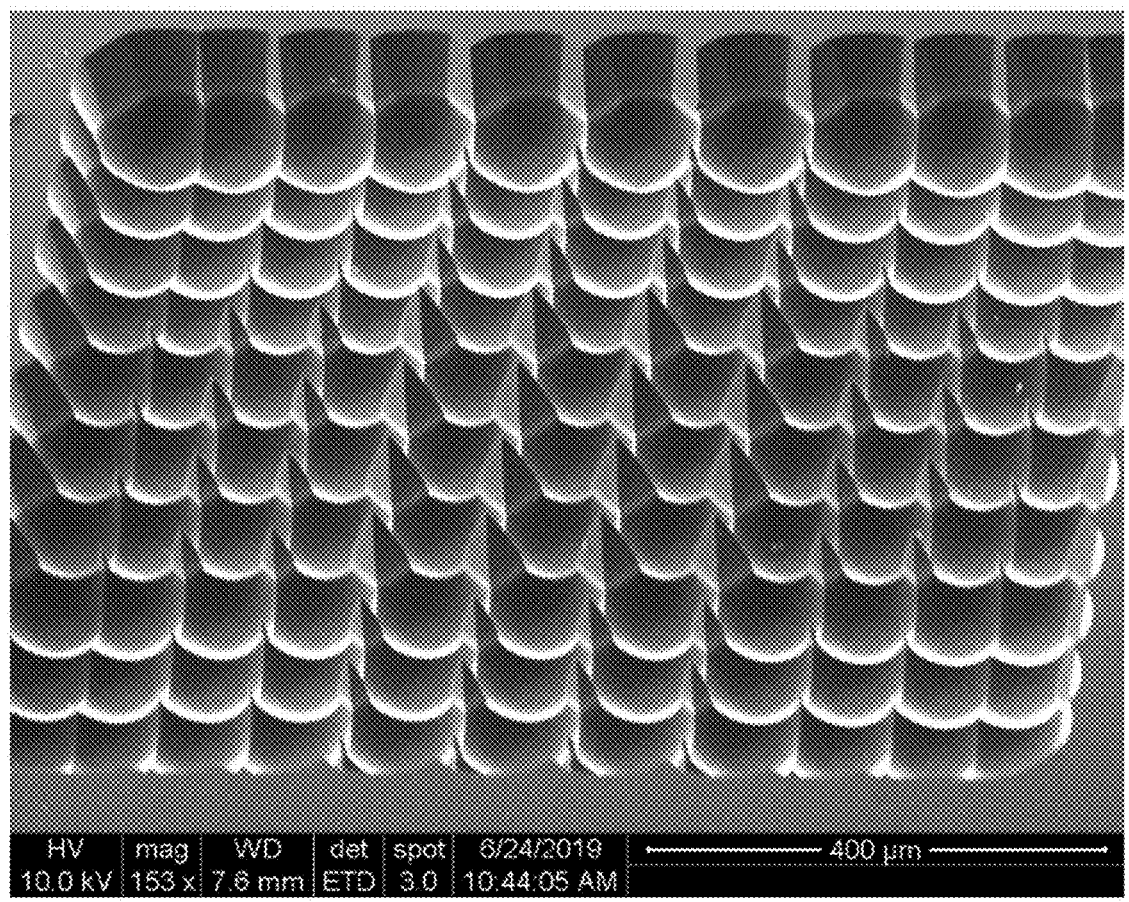

METHODS FOR MANUFACTURING HIGH-DENSITY NEURAL PROBES HAVING VARIOUS FORMS

CROSS-REFERENCE TO RELATED APPLICATION

This application claims under 35 U.S.C. § 119(a) the benefit of priority to Korean Patent Application No. 10-2020-0011815 filed on Jan. 31, 2020, the entire contents of which are incorporated herein by reference.

BACKGROUND

(a) Technical Field

The present disclosure relates to methods for manufacturing high-density neural probes having various forms and neural probes manufactured thereby.

(b) Background Art

Various methods for manufacturing neural probes which stimulate neurons and extract electrical signals therefrom have been developed to date. Thereamong, there is a conventional method for manufacturing a neural probe in which 3-D electrodes are manufactured by forming silicon pillars using a dicing saw and then wet-etching the silicon pillars, but this method is disadvantageous in that it is difficult to manufacture a high-density and small-sized 3D neural probe due to the size and the moving width of the dicing saw. Further, there is another method for manufacturing a neural probe in which 3D electrodes having an arrowhead structure are manufactured by forming holes in the form of arrowheads having sharp tips by etching a silicon base material using (a) dry and/or wet etching process(es) and then filling the holes with a metal, a conductive polymer or polycrystalline silicon, but this method is disadvantageous in that the slope and the form of the arrowheads due to the lattice preferred orientation of silicon cannot be adjusted, and thus, it is difficult to manufacture electrodes in various forms having sharp slopes. Further, there is a further method for manufacturing a neural probe by forming grooves in a checkerboard pattern through cutting using a diamond blade, but this method is disadvantageous in that the distance between micro-electrodes formed through cutting using the diamond blade is determined depending on the width of the blade and thus it is difficult to manufacture electrode patterns having a narrow gap therebetween, and it is difficult to integrate electrodes having different heights in one process.

Therefore, development of methods for manufacturing high-density and small-sized 3D neural probes, which include needles having sharp slopes and various heights, is required at present.

The above information disclosed in this Background section is only for enhancement of understanding of the background of the invention and therefore it may contain information that does not form the prior art that is already known in this country to a person of ordinary skill in the art.

RELATED ART DOCUMENT

Patent Document (Patent Document 1) Korean Patent Registration No. 10-1209403

SUMMARY OF THE DISCLOSURE

The present invention has been made in an effort to solve the above-described problems associated with the prior art, and it is an object of the present invention to provide a method for manufacturing a neural probe by patterning a base material through a photolithography process, forming trenches using anisotropic etching, and performing isotropic etching of the trenches.

It is another object of the present invention to provide a neural probe including a plurality of needles having various forms, which is manufactured by the above-described method.

In one aspect, the present invention provides a method for manufacturing a neural probe, including preparing a mask including a plurality of patterns, coating a base material with a photoresist, patterning the base material coated with the photoresist through a photolithography process using the mask, forming trenches by performing anisotropic etching of the patterned base material, and performing isotropic etching of the formed trenches.

In a preferred embodiment, the performing the isotropic etching may include removing the photoresist from one surface of the base material provided with the trenches formed therein, bonding another base material coated with a photoresist to a remaining surface of the base material provided with the trenches formed therein, and performing the isotropic etching of the trenches formed in the one surface of the base material.

In another preferred embodiment, the patterns may have at least one shape selected from the group consisting of polygonal shapes and circular shapes.

In still another preferred embodiment, the polygonal shapes may include at least one selected from the group consisting of a triangle, a diamond, a pentagon, a trapezoid and a cross.

In yet another preferred embodiment, the circular shapes may include at least one selected from the group consisting of a circle and an oval.

In still yet another preferred embodiment, the patterns may be arranged so as to be spaced apart from each other by a constant gap.

In a further preferred embodiment, the gap between the patterns may be within a range of 1-1,000 μm.

In another further preferred embodiment, sizes of the patterns may be within a range of 1-1,000 μm.

In another aspect, the present invention provides a neural probe including a plurality of needles having various forms, manufactured by the above-described method.

In a preferred embodiment, heights of the needles may be within a range of 1-5,000 μm.

In another preferred embodiment, sizes of the needles may be within a range of 1-1,000 μm.

Other aspects and preferred embodiments of the invention are discussed infra.

The above and other features of the invention are discussed infra.

BRIEF DESCRIPTION OF THE DRAWINGS

The above and other features of the present invention will now be described in detail with reference to certain exemplary embodiments thereof illustrated in the accompanying drawings which are given hereinbelow by way of illustration only, and thus are not limitative of the present invention, and wherein:

FIG. 1 is a flowchart briefly illustrating a method for manufacturing a neural probe according to one embodiment of the present invention;

FIG. 2 is a top view of a mask according to one embodiment of the present invention, illustrating a plurality of circular patterns formed on the mask so as to have a constant size and to be spaced apart from each other by a constant gap;

FIGS. 3(a) and 3(b) are a cross-sectional view and an SEM image of trenches formed by performing anisotropic etching of photoresist-removed regions of a patterned base material according to one embodiment of the present invention;

FIGS. 4(a) and 4(b) are a cross-sectional view and an SEM image of the trenches after performing isotropic etching according to one embodiment of the present invention;

FIG. 5 is an SEM image of a neural probe including a plurality of needles having various forms manufactured by the method according to the present invention;

FIG. 6 is a table showing patterns having various shapes and SEM images of neural probe needles manufactured using these patterns, when masks including the patterns having these shapes and arranged in various structures are used according to Example 2 of the present invention;

FIGS. 7(a) to 7(c) are SEM images of neural probe needles manufactured by varying the size of patterns according to Example 3 of the present invention;

FIG. 8 is a graph showing the heights of needles included in neural probes manufactured by varying the size and cycles of patterns according to Example 4 of the present invention; and FIG. 9 is an SEM image of a neural probe including a plurality of needles having various forms manufactured according to Example 5 of the present invention.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes, will be determined in part by the particular intended application and use environment.

In the figures, reference numbers refer to the same or equivalent parts of the present invention throughout the several figures of the drawings.

DETAILED DESCRIPTION

Advantages and features of the present invention and methods for achieving them will become apparent from the descriptions of aspects herein below with reference to the accompanying drawings. However, the present invention is not limited to the aspects disclosed herein but may be implemented in various different forms. The aspects are provided to make the description of the present invention thorough and to fully convey the scope of the present invention to those skilled in the art. It is to be noted that the scope of the present invention is defined only by the claims. In the following description of the embodiments, the same or similar elements are denoted by the same reference numerals even though they are depicted in different drawings.

In the following description of the embodiments, terms, such as "comprising", "including", "having", etc., will be interpreted as indicating the presence of characteristics, numbers, steps, operations, elements or parts stated in the description or combinations thereof, and do not exclude the presence of one or more other characteristics, numbers, steps, operations, elements, parts or combinations thereof, or possibility of adding the same. In addition, it will be understood that, when a part, such as a layer, a film, a region or a plate, is said to be "on" another part, the part may be located "directly on" the other part or other parts may be interposed between both parts. In the same manner, it will be understood that, when a part, such as a layer, a film, a region or a plate, is said to be "under" another part, the part may be located "directly under" the other part or other parts may be interposed between both parts.

All numbers, values and/or expressions representing amounts of components, reaction conditions, polymer compositions and blends used in the description are approximations in which various uncertainties in measurement generated when these values are acquired from essentially different things are reflected and thus, it will be understood that they are modified by the term "about", unless stated otherwise. In addition, it will be understood that, if a numerical range is disclosed in the description, such a range includes all continuous values from a minimum value to a maximum value of the range, unless stated otherwise. Further, if such a range refers to integers, the range includes all integers from a minimum integer to a maximum integer, unless stated otherwise.

In the following description of the embodiments, it will be understood that, when the range of a variable is stated, the variable includes all values within the stated range including stated end points of the range. For example, it will be understood that a range of "5 to 10" not only includes values of 5, 6, 7, 8, 9 and 10 but also includes arbitrary subranges, such as a subrange of 6 to 10, a subrange of 7 to 10, a subrange of 6 to 9, a subrange of 7 to 9, etc. and arbitrary values between integers which are valid within the scope of the stated range, such as 5.5, 6.5, 7.5, 5.5 to 8.5, 6.5 to 9, etc. Further, for example, it will be understood that a range of "10% to 30%" not only includes all integers including values of 10%, 11%, 12%, 13%, ... 30% but also includes arbitrary subranges, such as a subrange of 10% to 15%, a subrange of 12% to 18%, a subrange of 20% to 30%, etc., and arbitrary values between integers which are valid within the scope of the stated range, such as 10.5%, 25.5%, etc.

Method for Manufacturing Neural Probe

FIG. 1 is a flowchart briefly illustrating a method for manufacturing a neural probe according to one embodiment of the present invention. Referring to FIG. 1, the method includes preparing a mask including a plurality of patterns (S10), coating a base material with a photoresist (PR) (S20), patterning the base material coated with the photoresist through a photolithography process using the mask (S30), forming trenches by performing anisotropic etching of the patterned base material (S40), and performing isotropic etching of the formed trenches (S50).

In the preparation of the mask (S10), the mask including the patterns may be prepared in preparation for patterning the mask through the photolithography process.

The mask according to the present invention may be a photomask and, for example, a photomask including a plurality of patterns may be manufactured using an E-beam on a glass substrate formed of quartz ($SiO_2$) having high purity. Further, the size of the photomask may be greater than the size of the base material in order to prevent deformation of the shape of the patterns. The reason for this is that, if the size of the photomask is greater than the size of the base material, when size reduction is performed, the size of dust particles on the mask is reduced to that extent, and thus the malfunction of a circuit may be prevented.

The mask according to one embodiment may include a plurality of patterns. These patterns are not particularly limited as long as they may sharp and long needles in a central region formed by four trenches by etching the base material subsequently formed through the photolithography process.

The patterns included in the mask according to the present invention may be conventional patterns having various shapes capable of being in the present invention and, for example, may have at least one shape selected from the group consisting of polygonal shapes and circular shapes, and in more detail, the polygonal shapes may include at least one selected from the group consisting of a triangle, a diamond, a pentagon, a trapezoid and a cross, and the circular shapes may include at least one selected from the group consisting of a circle and an oval. Particularly, the patterns included in the mask may include circular patterns, without being limited thereto. When the circular patterns are used, it is favorable to form needles in the form of arrowheads, the surface area of electrodes is increased, and thus impedance may be reduced.

FIG. 2 is a top view of the mask according to one embodiment of the present invention, illustrating a plurality of circular patterns formed on the mask so as to have a constant size and to be spaced apart from each other by a constant gap. Referring to this figure, a circle indicated by a solid line represents a circular mask pattern, and a circle indicated by a dotted line represents an extended region which is subsequently etched through an etching process. Here, the gap between the respective patterns may be a distance between two curved surfaces, a distance between two vertices, a distance between a line segment and a vertex (the length of a straight line perpendicular to the line segment up to the vertex) or a distance between two line segments, and the gap may be in the range of 1-1,000 μm, preferably in the range of 10-100 μm. When the gap is less than 1 μm, a silicon base material between the patterns is etched and thus it is difficult to form needles, and when the gap exceeds 1,000 μm, a depth in isotropic etching is increased. Further, the size of the patterns may be a horizontal width, a vertical width or a diagonal width, without being limited to a specific width, and may be in the range of 1-1,000 μm, preferably in the range of 10-100 μm. When the size is less than 1 μm, it is difficult to manufacture deep trenches, and when the size exceeds 1,000 μm, it is difficult to manufacture a high-density needle array.

That is, the present invention may implement probe structures having various forms depending on the design of patterns included in a mask, and manufacture neural probes having different heights by adjusting the height of needles included in the probes because an etching tendency is varied by adjusting the size of patterns and the gap between the patterns.

In the coating of the base material with the photoresist (PR) (S20), the base material is coated with a photoresist, which is sensitive to light, in preparation for patterning through the photolithography process.

The base material according to the present invention may be one of generally known wafers which can be used to perform the photolithography process, for example, various semiconductor wafers, such as a silicon wafer, a silicon-on-insulator (SOI) wafer, a Ge wafer, a GaAs wafer, etc., even though the type and the density of a dopant configured to dope a wafer are changed, and preferably be a highly doped SOI wafer, without being limited to a specific wafer. The highly doped SOI wafer may easily reduce impedance of electrodes and electrically isolate the electrodes.

In the present invention, the base material may be coated with the photoresist using a spin coating method, a dip coating method, etc., and be preferably coated with the photoresist using the spin coating method which is generally used, without being limited to a specific method.

Therefore, the photoresist coated on the base material according to the present invention may be highly sensitive to ultraviolet light. Further, the photoresist according to the present invention may be a positive photoresist or a negative photoresist, and is preferably a positive photoresist so as to remove only parts of the photoresist exposed to light and then to perform isotropic etching using the remainder of the photoresist, without being limited to a specific kind. Further, the photoresist may be coated on the base material to a uniform and thin thickness in order to perform fine patterning through the photolithography process, and preferably, the coating thickness of the photoresist may be 2-10 μm. When the coating thickness of the photoresist is less than 2 μm, it is difficult to perform masking during the etching process, and when the coating thickness of the photoresist exceeds 10 μm, it is difficult to perform fine patterning.

In the patterning of the base material coated with the photoresist through the photolithography process (S30), the base material coated with the photoresist is patterned through an exposure process and a development process using the mask.

In the patterning of the base material, the exposure process in which light is radiated onto the photoresist is performed. That is, when the mask is placed on the base material coated with the photoresist and then light is radiated thereto, light passing through the patterns included in the mask may transfer the patterns to the surface of the base material. Here, a stepper, a contact aligner or the like may be used as an exposure apparatus.

Thereafter, the development process, in which a developer is sprayed onto the base material coated with the photoresist so as to selectively remove regions of the photoresist which are exposed to light or regions of the photoresist which are not exposed to light, is performed. In the development process according to the present invention, the photolithography process may be performed on the base material coated with a positive photoresist, and thereby, the regions of the photoresist which are not exposed to light may remain after the process and the regions of the photoresist which are exposed to the light may be removed by the developer.

In the formation of the trenches (S40), the trenches are formed in the base material by performing anisotropic etching of the base material patterned through the photolithography process. Referring to FIG. 2, anisotropic etching is performed in the downward direction of the patterns indicated by the solid line.

FIGS. 3(*a*) and 3(*b*) are a cross-sectional view and an SEM image of trenches formed by performing anisotropic etching of the photoresist-removed regions of the patterned base material according to the present invention. Referring to these figures, such anisotropic etching may be performed using dry etching or wet etching, and is preferably formed through dry etching so as to achieve fine patterning and improve a yield. The dry etching may be deep reactive ion etching (DRIE) as a physical and chemical etching process, chemical vapor etching as a chemical etching process, or sputtering or ion milling as a physical etching process, and the anisotropic etching is preferably performed through a DRIE process, in which etching may be performed at a high selectivity and a high etch rate, without being limited to a specific process. Further, in the DRIE process, the depth of trenches may be adjusted in consideration of an etch rate, and the height of needles which are finally manufactured may be adjusted depending on the depth of the trenches. Therefore, the depth of the trenches formed by etching may be 1-5,000 µm. The depth of the trenches may vary according to the intended use of the neural probe.

That is, in the manufacturing method according to the present invention, anisotropic etching is performed through the DRIE process and the depth of the trenches is adjustable in consideration of the etch rate, and thus a neural probe including needles in the form of sharper arrowheads compared to those obtained through conventional manufacturing methods, and the neural probe manufactured thereby may more effectively penetrate brain tissue, record neural signals from the brain and transmit electrical stimulation to the brain.

In the performance of isotropic etching (S50), a plurality of needles is formed by performing isotropic etching of the formed trenches.

The performance of isotropic etching according to the present invention may include removing the photoresist from one surface of the base material provided with the trenches formed therein, bonding another base material coated with a photoresist to the other surface of the base material provided with the trenches formed therein, and performing isotropic etching of the trenches formed in the one surface of the base material.

In more detail, the photoresist may be removed from one surface of the base material provided with the trenches formed therein in order to increase isotropy of etching and thus to sharpen the tips of needles. Thereafter, in order to more effectively perform the subsequent isotropic etching process, in which the temperature of the base material is increased, a bonding process may be performed. More particularly, another base material, configured to support the base material provided with the trenches formed therein, is coated with the photoresist using the spin coating method, and the base material provided with the trenches formed therein is placed on the base material coated with the photoresist. Thereafter, isotropic etching is performed in the trenches formed in the one surface of the base material, and thereby, the neural probe including the needles may be manufactured.

Here, such isotropic etching may be performed using dry etching or wet etching, and is preferably formed through dry etching so as to achieve fine patterning and improve a yield. Dry etching may be deep reactive ion etching (DRIE) as a physical and chemical etching process, chemical vapor etching as a chemical etching process, or sputtering or ion milling as a physical etching process, and the isotropic etching is preferably performed through a DRIE process, in which etching may be performed at a high selectivity and a high etch rate, without being limited to a specific process. Here, when the isotropic etching is performed through the DRIE process, referring to FIG. 2 and FIGS. 4(a) and 4(b), etching is carried out not only in the vertical direction but also in the horizontal direction so as to etch up to circular regions, indicated by the dotted line, on the base material and thus, the base material in a region between the trenches is removed. Thereby, a neural probe structure including needles having a unique form, each of which is formed in a central region formed by four trenches, may be manufactured, and thus, an etching tendency may be varied depending on the size of patterns and the gap between the patterns.

Therefore, according to the present invention, the height of finally manufactured needles may be adjusted, and preferably, more sharp needles may be manufactured, and thus, a micro-neural probe which may more effectively penetrate brain tissue, record neural signals from the brain and transmit electrical stimulation to the brain may be manufactured. Further, the method according to the present invention, in which only the photolithography process and the etching process are used, simplifies a manufacturing process of the neural probe, minimizes changes in the characteristics of the neural probe depending on process equipment or conditions, and may thus ensure a high yield, thereby being advantageous in terms of commercialization.

Neural Probe

FIG. 5 is an SEM image of a neural probe including a plurality of needles having various forms manufactured by the method according to the present invention. Referring to this figure, it may be confirmed that the neural probe according to the present invention includes needles having a sharper form than the conventional neural probes. The heights of the needles may be 1-5,000 µm, preferably 100-5,000 µm. Further, the sizes of the needles may be 1-1,000 µm. When the height of the needles is less than 1 µm, no needles may be formed through isotropic etching, and when the height of the needles exceeds 5,000 µm, an etching time may be excessively increased. Further, when the size of the needles is less than 1 µm, no needles may be formed through isotropic etching, and when the size of the needles exceeds 1,000 µm, it is difficult to form a high-density needle array.

That is, the neural probe according to the present invention may include sharp and long needles so as to effectively penetrate brain tissue, record neural signals from the brain and transmit electrical stimulation to the brain and to minimize tissue damage, and adjust the height of the needles by adjusting the size of the patterns and the gap between the patterns and thus include the needles having different heights, thereby being capable of being designed to be optimized for the distribution or form of tissue cells, thus maximizing the performance of the neural probe.

The following examples illustrate the invention and are not intended to limit the same. These examples are merely examples to aid in understanding of the present invention, and the scope of the invention is not limited thereby.

Example 1: Neural Probe Including Needles (S10) A photomask which includes a plurality of patterns formed on a glass substrate formed of quartz ($SiO_2$) using an E-beam was prepared as the mask used in the present invention. As the patterns included in the photomask, circular patterns were arranged adjacent to each other. Here, the gap between the respective patterns was 30 µm, and the size of the patterns was 70 µm.

(S20) A silicon wafer was prepared as the base material used in the present invention, and was coated with a negative photoresist using the spin coating method. Here, the coating thickness of the photoresist was 5 µm.

(S30) The photolithography process was performed by radiating light to the base material coated with the photoresist at an intensity of 22 mW/cm 2 for 12.4 seconds using the photomask by a contact aligner. Thereafter, regions of the photoresist which were not exposed to the light were removed by spraying a developer onto the base material.

(S40) Trenches were formed by performing anisotropic etching of regions of the patterned base material, in which the photoresist is removed, through dry etching, i.e., the deep reactive ion etching (DRIE) process which is a physical and chemical etching process. Here, the depth of the trenches was 164 µm.

(S50) The photoresist was removed from one surface of the base material provided with the trenches formed therein through an oxygen plasma ashing method. Thereafter, another base material, configured to support the base material provided with the trenches formed therein, is coated with a photoresist using the spin coating method, the base material provided with the trenches formed therein through the DRIE process was placed on the base material coated with the photoresist, and bonding between the two base materials using the photoresist was completed. Thereafter, the neural probe including a plurality of needles in the form of sharp arrowheads, as shown in FIG. 5, was manufacturing by performing isotropic etching of the trenches formed in the one surface of the base material through the DRIE process.

Example 2: Neural Probe Including Needles Having Form Varied Depending on Shape of Patterns Compared to Example 1, neural probes were manufactured in the same manner as in Example 1 except that masks including patterns having shapes other than a circular shape were used, as shown in FIG. 6.

Example 3: Neural Probe Including Needles Having Height Varied Depending on Size of Patterns Compared to Example 1, neural probes were manufactured in the same manner as in Example 1 except that masks including patterns having circular shapes having sizes (diameters) of 50 μm, 70 μm and 100 μm, respectively, were used.

Example 4: Neural Probe Including Needles Having Height Varied Depending on Gap Between Patterns Compared to Example 1, neural probes were manufactured in the same manner as in Example 1 except that masks including patterns having gaps of 30 μm (at 150 and 170 cycles) and 50 μm (at 170 and 200 cycles), respectively, were used.

Example 5: Neural Probe Including Needles Having Different Heights Depending on Sizes of Patterns and Gaps Between Patterns Compared to Example 1, a neural probe was manufactured in the same manner as in Example 1 except that a mask having one pattern array including a plurality of patterns having various sizes and various gaps therebetween was used. The shapes of the patterns were a circle, a rectangle, a pentagon, a cross and the like, and the needle array including needles having heights within the range of 10-110 μm was manufactured using one pattern array by adjusting the gaps between the patterns within the range of 10-50 μm and adjusting the sizes of the patterns within the range of 50-100 μm.

Test Example 1: Observation of Form of Needles of Neural Probe Depending on Shape of Patterns Included in Mask In the neural probes manufactured using the masks including the patterns having various shapes according to Example 2, the forms of the needles of the neural probes which were finally manufactured were observed, as shown in FIG. 6.

As a result, it may be confirmed from FIG. 6 that neural probes including a plurality of needles, of which the form, size and gap therebetween were varied depending on the shape and the arrangement of the patterns included in the mask, may be manufactured.

Therefore, it will be understood that a neural probe including a plurality of needles having a desired form, size and gap therebetween may be manufactured depending on the shape and the arrangement of patterns included in a mask.

Test Example 2: Observation of Height of Needles of Neural Probe Depending on Shape of Patterns and Gap Between Patterns Included in Mask FIGS. 7 to 9 illustrate the SEM images of the neural probes manufactured using the masks including the patterns according to Examples 2 and 3, and the heights of the needles of the neural probes.

As a result, it may be confirmed from FIG. 7(a)~FIG. 7(c) that, as the size of the patterns (i.e., the diameter of the circular patterns) is increased, the height of the needles is increased according to Example 3. Further, it may be confirmed from FIG. 8 that, as the gap between the patterns is increased, the height of the needles is increased. In addition, it may be confirmed from FIG. 8 that, when the gap between the patterns is 30 μm, as the number of cycles is increased, the height of the needles is increased, but when the gap between the patterns is 50 μm, as the number of cycles is increased, the height of the needles is decreased. Therefore, it will be understood that, when the gap between the patterns is 50 μm, the height of the needles may be more effectively improved at about 170 cycles under the same pattern size conditions. Further, referring FIG. 8, as a result of manufacture of the neural probe by varying both the size of the patterns and the gap between the patterns included in the mask, it may be confirmed that one neural probe may include a plurality of needles having various forms and various heights.

Therefore, the neural probe manufactured by the method according to the present invention may implement needles having various forms, and include a plurality of needles having different heights by adjusting the size of the patterns and the gap between the patterns. Therefore, the neural probe according to the present invention may be designed so as to be optimized for the distribution or the form of tissue cells, thus maximizing the performance thereof. The neural probe manufactured by the method according to the present invention is applicable to neural probe manufacturing technology which is core technology in neuroprosthetics, and may extend to other various fields, such as micro-needles used to inject drugs, probes of atomic force microscopes (AFMs), super-hydrophobic films, etc.

As is apparent from the above description, a method for manufacturing a neural probe according to the present invention, in which only a photolithography process and an etching process are used, simplifies a manufacturing process of the neural probe, minimizes changes in the characteristics of the neural probe depending on process equipment or conditions, and may thus ensure a high yield, thereby being advantageous in terms of commercialization. Further, in the method according to the preset invention, needles in the form of sharp arrowheads may be easily manufactured through a deep reactive ion etching (DRIE) process and pattern technology, and thus, a micro-neural probe which minimizes tissue damage may be manufactured. In addition, various forms of needles may be implemented depending on the shape of patterns included in a mask, the height of the needles included in the probe may be controlled by adjusting the size of the patterns and the gap between the patterns, and thereby, a neural probe having a plurality of needles having different heights may be manufactured. Therefore, the neural probe according to the present invention may be designed so as to be optimized for the distribution or the form of tissue cells, thus maximizing the performance of the neural probe. Moreover, the neural probe according to the present invention is applicable to neural probe manufacturing technology which is core technology in neuroprosthetics, and may be extend to other various fields, such as micro-needles used to inject drugs, probes of atomic force microscopes (AFMs), super-hydrophobic films, etc.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A method for manufacturing a neural probe array, the method comprising:
    preparing a mask comprising a plurality of patterns;
    coating a first base material with a photoresist;
    patterning the first base material coated with the photoresist through a photolithography process using the mask;
    forming trenches in the first base material by performing an anisotropic etching of the patterned first base material; and
    performing an isotropic etching of the formed trenches;
    wherein the patterns are arranged so as to be spaced apart from each other by gaps,
    wherein the gaps between the patterns are in a range of 10-200 µm;
    wherein performing the isotropic etching of the trenches comprises: removing the photoresist from the surface of the first base material provided with the trenches formed therein; bonding a second base material coated with a photoresist to a surface of an opposite side of the first base material provided with the trenches formed therein; and performing the isotropic etching of the trenches formed in the surface of the first base material, thereby, forming the neural probe array comprising a plurality of needles having sharp tips.

2. The method of claim 1, wherein the patterns have at least a shape selected from a group consisting of polygonal shapes and circular shapes.

3. The method of claim 2, wherein the polygonal shapes comprise at least one selected from the group consisting of a triangle, a diamond, a pentagon, a trapezoid and a cross.

4. The method of claim 2, wherein the circular shapes comprise at least one selected from a group consisting of a circle and an oval.

5. The method of claim 2, wherein sizes of the patterns are within a range of 1-1,000 µm.

* * * * *